United States Patent [19]

Franz et al.

[11] Patent Number: 4,545,804

[45] Date of Patent: Oct. 8, 1985

[54] N(AMINOPHOSPHINYLMETHYL) GLYCINE DERIVATIVES

[75] Inventors: John E. Franz, Crestwood; Robert J. Kaufman, University City, both of Mo.

[73] Assignee: Monsanto Company, St. Louis, Mo.

[21] Appl. No.: 553,597

[22] Filed: Nov. 21, 1983

[51] Int. Cl.$^4$ .................. E05B 65/46; C07F 9/22
[52] U.S. Cl. ............................ 71/86; 560/169
[58] Field of Search ................. 560/169; 71/86

[56] References Cited

U.S. PATENT DOCUMENTS

| | | | |
|---|---|---|---|
| 3,799,758 | 3/1974 | Franz | 71/86 |
| 4,180,394 | 12/1979 | Franz et al. | 71/86 |
| 4,251,258 | 2/1981 | Kaufman | 71/87 |
| 4,312,662 | 1/1982 | Gaertner | 71/86 |
| 4,353,731 | 10/1982 | Franz | 560/169 |
| 4,359,332 | 11/1982 | Franz | 560/169 |

FOREIGN PATENT DOCUMENTS 2094313 9/1982 United Kingdom ............ 71/86

*Primary Examiner*—Michael L. Shippen
*Attorney, Agent, or Firm*—D. Bennett; A. H. Cole; Paul D. Matukaitis

[57] ABSTRACT

Novel N(aminophosphinylmethyl)glycine derivatives are described that show significant herbicidal activity.

6 Claims, No Drawings

N(AMINOPHOSPHINYLMETHYL) GLYCINE DERIVATIVES

BACKGROUND TO THE INVENTION

This invention relates to certain novel phosphinylmethylglycine derivatives and to methods of preparing such derivatives. Compounds of the invention have been found to have significant herbicidal activity with respect to both narrow and broadleaf plants. They are therefore useful as nonselective post-emergent herbicides.

DESCRIPTION OF THE INVENTION

The novel compounds of the invention have the general formula:

wherein:
(a) R is selected from substituted and unsubstituted $C_1$ to $C_{10}$ alkyl and alkyloxyalkyl groups; and
(b) Each $R^1$ is individually selected from hydrogen and $C_1$ to $C_6$ alkyl groups; and
(c) each $R^2$ is individually selected from hydrogen and $C_1$ to $C_6$ alkyl groups.

In the above formula R can be, for example, hydrogen methyl, ethyl, isopropyl, n-propyl, n-butyl, sec-butyl, tert-butyl, hexyl, octyl, 2-ethylhexyl, decyl, 2-chloropropyl, 1-chloro-sec-butyl, 2,3-dichloropentyl, 2,4,6-trichlorodecyl, ethoxyhexyl, methoxyoctyl, methoxyethyl or methoxymethyl.

The group $-NR^1R^2$ can be, for example, such groups as methylamino; ethylamino; isopropylamino; tert-butylamino; sec-butylamino; pentylamino; n-hexylamino; 3-ethyl butylamino; dimethylamino; N-methyl, N-propylamino; N-methyl, N-hexylamino; and N,N-dipropylamino.

Typical compounds according to the invention include glycine, N-(bis(dimethylamino)phosphinylmethyl), ethyl ester; glycine, N-(bis(ethylamino)phosphinylmethyl), n-propyl ester; glycine, N-bis(isopropylamino)-phosphinylmethyl), 2-ethyl butyl ester; and glycine, N-(bis[(1-methylethyl)-amino]phosphinylmethyl), ethyl ester.

The invention also comprises a process for the production of the novel compounds of the invention which comprises reducing a compound having the general formula:

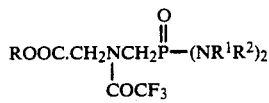

using an alkali metal borohydride wherein R, $R^1$, and $R^2$ have the significances indicated above.

The trifluoroacetyl derivative reduced as described above can be obtained from glyphosate (i.e. N-phosphonomethylglycine) by reaction with an alcohol in the presence of hydrogen chloride to produce the monoester hydrochloride salt. From this salt the monoester can be isolated by reaction with propylene oxide in alcohol. This ester is then reacted with trifluoroacetic anhydride and trifluoroacetic acid followed by thionyl chloride, to generate the N-trifluoro-acetyl derivative of the N-(methyldichlorophosphinyl)glycine ester. The starting material used in the process of the invention can be obtained by reacting this trifluoroacetyl derivative with a compound $HNR^1R^2$, (where $R^1$ and $R^2$ have the significances set forth above), in tetrahydrofuran and in the presence of a proton acceptor such as a tertiary amine.

The process of the reaction is preferably carried out at a temperature of from 0° C. to 25° C. and in solution in a hydroxyl group containing organic solvent such as ethyl alcohol, isopropyl alcohol, ethylene chlorohydrin or the like. The most preferred temperature is room temperature and the solvent of choice is most commonly ethyl alcohol.

The borohydride used to accomplish the reduction is added to the reaction in a roughly molar equivalent amount to that of the trifluoroacetyl derivative. The reaction progresses relatively efficiently such that a large molar excess of the borohydride is not normally required.

The compounds that may provide the starting materials for the production of the compounds according to the present invention are described in U.S. Pat. No. 4,199,345. This application also teaches a process for the preparation of such intermediates. The teachings of U.S. Pat. No. 4,199,345 are incorporated by this reference into the present application.

The alkali metal borohydride is conveniently sodium borohydride though, if desired, the potassium, lithium or other alkali metal salt can be substituted.

DESCRIPTION OF THE PREFERRED EMBODIMENTS

The invention is now further described with reference to the following examples which are for the purpose of illustration only and are intended to imply no necessary limitation on the essential scope of the invention.

EXAMPLE 1

A solution of 3.0 g. (0.0086 mole) of the ethyl ester of N-trifluoroacetyl[bis(dimethylamino)phosphinylmethyl]glycine in approximately 20 ml. of distilled ethanol was added to a reaction vessel followed by 0.33 g. (0.0086 mole) of sodium borohydride dissolved in a further 20 ml. of distilled ethanol. Addition of the borohydride was accompanied by good stirring.

The reaction was allowed to continue at room temperature for 20 minutes after which the ethanol was stripped off at reduced pressure and the residue was quenched with about 20 ml. of water. Sodium chloride was added to give a saturated solution from which the product was extracted twice using ethyl acetate. The second ethyl acetate extractant solution was dried over magnesium sulfate, the magnesium sulfate was removed by filtration and the solution was concentrated by heating in vacuo.

The reaction yield was 1.19 g of a light yellow oil. The product was analyzed using NMR and infra-red spectroscopic techniques. The results were consistent with the structure:

There was some indication, from the NMR evidence, of the formation of a small amount of the corresponding animal as a by-product.

EXAMPLE 2

A reaction vessel was charged with a solution in 80 ml. of distilled ethanol of 4.55 g (0.01212 mole) of the ethyl ester of N-trifluoroacetyl[bis(isopropylamino)-phosphinylmethyl]glycine.

To this solution was added, with stirring, a solution of sodium borohydride in 20 ml. distilled ethanol. The reaction was allowed to proceed at room temperature under a drying tube for 25 minutes before the reaction mixture was concentrated in vacuo to remove some of the alcohol.

The residue was quenched with about 35 ml. of water double extracted with distilled ethyl acetate and the extractant dried over magnesium sulfate. The magnesium sulfate was filtered off and the filtrate was concentrated using a kugelrohr apparatus. The yield was 1.6 g.

The product was somewhat impure and in an attempt to remove some of the impurities, the product was triturated with ether. The ether-insoluble portion of the product when analyzed using NMR spectroscopy, gave a result consistent with the structure,

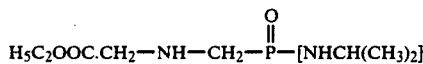

EXAMPLE 3

This example illustrates the post-emergent herbicidal activity of the compounds produced in Examples 1 and 2, designated A and B respectively.

In each case the compound (A or B) was applied in spray form to about 14–21 day old specimens of the various plant species indicated in Table I (below).

The additive was incorporated in a spray solution comprising 3 parts of cyclohexanone and 1 part of a surfactant (35 parts of the butylamine salt of dodecylbenzenesulfonic acid and 65 parts of tall oil condensed with ethylene oxide in the ratio of 11 moles of ethylene oxide to 1 mole of tall oil). The spray was made up just prior to application to the plants by diluting an ethanol-based solution of each additive using tetrahydrofuran.

The application rate of the spray was varied as indicated the the treated plants were placed in a greenhouse in good growing conditions. After the indicated period the effect on the plants was examined and rated according to the following index.

0 indicates less than 25% inhibition
1 indicates 25 to 49% inhibition
2 indicates 50 to 74% inhibition
3 indicates 75 to 99% inhibition
4 indicates 100% inhibition The plant species tested are indicated by letter, the significances of which are as follows:

A. Canada Thistle*
B. Common Cocklebur
C. Velvetleaf
D. Morningglory
E. Common Lambsquarters
F. Pennsylvania Smartweed
G. Nutsedge(yellow)*
H. Quackgrass
I. Johnsongrass*
J. Bromus Tectorum*
K. Barnyardgrass
L. Soybean
M. Sugar Beet
N. Wheat
O. Rice
P. Sorghum
Q. Wild Buckwheat
R. Hemp Sesbania
S. Proso millet
T. Crabgrass

*Established from vegetative propagules

The results obtained were as shown in Tables I and II.

TABLE I

| | | | HERBICIDAL ACTIVITY | | | | | | | | | | |
|---|---|---|---|---|---|---|---|---|---|---|---|---|---|
| COMPOUND | APPLICATION RATE (kg/ha) | WAT[1] | A | B | C | D | E | F | G | H | I | J | K |
| A | 11.2 | 2 | 3 | 3 | 3 | 3 | 4 | 4 | 2 | 3 | 3 | 3 | 3 |
|   |      | 4 | 4 | 3 | 4 | 4 | 4 | 4 | 3 | 4 | 4 | 4 | 4 |
|   | 5.6  | 2 | 2 | 2 | 2 | 2 | 3 | 3 | 1 | 4 | 1 | 2 | 3 |
|   |      | 4 | 2 | 2 | 4 | 3 | 4 | 4 | 2 | 4 | 2 | 3 | 4 |
| B | 11.2 | 2 | 3 | 3 | 3 | 4 | 4 | 4 | 1 | 3 | 4 | 3 | 4 |
|   |      | 4 | 3 | 3 | 4 | 4 | 4 | 4 | 1 | 4 | 4 | 4 | 4 |
|   | 5.6  | 2 | 2 | 2 | 1 | 3 | 4 | 3 | 1 | 1 | 0 | 1 | 3 |
|   |      | 4 | 4 | 3 | 3 | 4 | 4 | 4 | 2 | 1 | 0 | 4 | 3 |

TABLE II

| | | | HERBICIDAL ACTIVITY | | | | | | | | | | | | | |
|---|---|---|---|---|---|---|---|---|---|---|---|---|---|---|---|---|
| COMP | APPLIC RATE kg/ha | WAT[1] | L | M | N | O | P | B | Q | D | R | E | F | C | H | S | K | T |
| A | 5.6 | 2 | 3 | 4 | 4 | 4 | 3 | 3 | 2 | 3 | 4 | 4 | 3 | 3 | 3 | 4 | 3 | 4 |
|   | 5.6 | 4 | 3 | 4 | 4 | 4 | 4 | 3 | 3 | 3 | 4 | 4 | 4 | 4 | 3 | 4 | 4 | 4 |
|   | 1.12 | 2 | 2 | 3 | 3 | 2 | 2 | 2 | 1 | 2 | 3 | 3 | 2 | 2 | 1 | 3 | 3 | 3 |
|   | 1.12 | 4 | 2 | 3 | 3 | 2 | 1 | 2 | 1 | 2 | 3 | 4 | 3 | 3 | 1 | 3 | 3 | 4 |
| B | 1.12 | 2 | 2 | 3 | 2 | 3 | 2 | 2 | 2 | 3 | 1 | 2 | 2 | 2 | 2 | 3 | 3 | 3 |
|   | 1.12 | 4 | 1 | 3 | 2 | 4 | 3 | 3 | 1 | 3 | 1 | 2 | 3 | 2 | 3 | 4 | 4 | 4 |

[1]WAT = Weeks after treatment

From the illustrative data presented above, it should be clear that the herbicidal response will be dependent upon the compound employed, the rate of application, the plant specie involved and other factors well understood by those skilled in the art.

The herbicidal compositions, (including concentrates which require dilution prior to application to the plants), of this invention contain at least one active ingredient and an adjuvant in liquid or solid form. The compositions are prepared by admixing the active ingredient with an adjuvant such as a diluent, extender, carrier or conditioning agent to provide composition in the form of a finely-divided particulate solid, pellet, solution, dispersion or emulsion. Thus, the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent. However, it is found that not all the compounds are resistant to hydrolysis and in some cases this may dictate the use of nonaqueous solvent media.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, ditertiary acetylenic glycols; polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid)taurates.

Water-dispersible powder compositions can be made containing one or more active ingredients, an inert solid extender and one or more wetting and dispersing agents. Water-dispersible powders of this invention usually contain from about 5 to about 95 parts by weight of the active ingredient, from about 0.25 to 215 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspension can be prepared by mixing together and grinding an aqueous slurry of a water-insoluble active ingredient in the presence of a dispersing agent to obtain a concentrated slurry of very finely-divided particles. The resulting concentrated aqueous suspension is characterized by its extremely small particle size, so that when diluted and sprayed, coverage is very uniform. Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts of active ingredient, about 1 to 50 parts surface active ingredient, about 1 to 50 parts surface active agent about about 4 to 94 parts solvent, all parts being by weight based on the total weight of emulsifiable oil.

Although compositions of this invention can also contain other additaments, for example fertilizers, phytotoxicants and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, or other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include for example triazines, ureas, carbamates, acetamides, acetanilides, uracils, acetic acids, phenols, thiocarbamates, triazoles, benzoic acids, nitriles and the like such as:

3-amino-2,5-dichlorobenzoic acid
3-amino-1,2,4-triazole
2-methoxy-4-ethylamino-6-isopropylamino-s triazine
2-chloro-4-ethylamino-6-isopropylamino-s triazine
2-chloro-N,N-diallylacetamide
2-chloroallyl diethyldithiocarbamate
N'-(4-chlorophenoxy)phenyl-N,N-dimethylurea
2,2-dichloropropionic acid
S-2,3-dichloroallyl N,N-diisopropylthiol carbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidinium salt
3-(3,4-dichlorophenyl)-1,1-dimethylurea
4,6-dinitro-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha,alpha,alpha-trifluoro-2,6-dinitro-N,N-dipropylptoluidine
S-propyl dipropylthiolcarbamate
2-4-dichlorophenoxyacetic acid
N-isopropyl-2-chloroacetanilide
2',6'-diethyl-N-methoxymethyl-2-chloroacetanilide
monosodium acid methanearsonate
disodium methanearsonate
N-(1,1-dimethylpropynyl)-3,5-dichlorobenzamide Fertilizers useful in combination with the active ingredients include for example ammonium nitrate, urea, potash, and superphosphate.

When operating in accordance with the present invention, effective plant regulating amounts of the glycines are applied directly or indirectly to the plants. The application of liquid and particulate solid plant regulating compositions can be carried out by conventional methods, e.g. power dusters; boom, recirculating and hand sprayers; rope-wick applicators; and spray dusters. The compositions can also be applied from airplanes as a dust or a spray because of their effectiveness at low dosages. The application of a herbicidally effective amount of the compounds of this invention to the plant is essential and critical for the practice of the present invention. The exact amount of active ingredient to be employed is dependent upon the response desired in the plant as well as such other factors as the plant species, and the environmental conditions, as well as the specific compound employed. In general, the active ingredients are employed in herbicidally effective amounts equivalent to from about 0.112 to about 10.0 kg/hectare.

Although the invention is described with respect to specific modifications, the details thereof are not to be construed as limitations except to the extent indicated in the following claims.

What is claimed is:

1. A compound having the formula:

(a) R is selected from $C_1$ to $C_{10}$ alkyl, haloalkyl and alkyloxyalkyl groups;
(b) each $R^1$ is individually selected from hydrogen and $C_1$ to $C_6$ alkyl groups; and
(c) each $R^2$ is individually selected from hydrogen and $C_1$ to $C_6$ alkyl groups.

2. A compound according to claim 1 in which both $-NR^1R^2$ moieties are selected from the group consisting of dimethylamine, diisopropylamine, methylamine, ethylamine and isopropylamine.

3. Glycine, N-[bis(dimethylamino)phosphinylmethyl], ethyl ester.

4. Glycine, N-[bis(monoisopropylamino)phosphinylmethyl], ethyl ester.

5. A composition comprising a herbicidally effective amount of a compound according to claim 1 and an inert adjuvant.

6. A composition according to claim 5 in which the herbicidally effective compound is selected from the group consisting of the ethyl ester of N-[bis(dimethylamino)phosphinylmethyl]glycine and the ethyl ester of N-[bis(monoisopropylamino)phosphinylmethyl]glycine.

* * * * *